(12) United States Patent
Smith et al.

(10) Patent No.: US 7,888,318 B1
(45) Date of Patent: Feb. 15, 2011

(54) METHOD OF PREPARING AN ORGAN BY PERFUSION

(75) Inventors: Richard Anthony Godwin Smith, Cambridge (GB); Julian Roy Pratt, London (GB); Steven Howard Sacks, Kent (GB)

(73) Assignee: Adprotech Limited (GB)

( * ) Notice: Subject to any disclaimer, the term of this patent is extended or adjusted under 35 U.S.C. 154(b) by 0 days.

(21) Appl. No.: 09/936,205

(22) PCT Filed: Mar. 8, 2000

(86) PCT No.: PCT/GB00/00834
§ 371 (c)(1),
(2), (4) Date: Oct. 29, 2001

(87) PCT Pub. No.: WO00/53007
PCT Pub. Date: Sep. 14, 2000

(30) Foreign Application Priority Data
Mar. 10, 1999 (GB) .................. 9905503.0

(51) Int. Cl.
*A61K 38/00* (2006.01)

(52) U.S. Cl. .............. 514/12; 514/2; 530/350; 435/69.1

(58) Field of Classification Search .............. 435/69.1; 514/2, 12; 530/300, 350
See application file for complete search history.

(56) References Cited

U.S. PATENT DOCUMENTS

| | | | | |
|---|---|---|---|---|
| 5,693,462 | A | 12/1997 | Raymond | 435/1 |
| 5,702,881 | A | 12/1997 | Brasile et al. | 435/1.2 |
| 5,833,989 | A | 11/1998 | Mossakowska et al. | 424/185.1 |
| 5,843,778 | A | 12/1998 | Rosengard et al. | 435/325 |
| 5,847,082 | A | 12/1998 | Rother et al. | 530/350 |
| 6,193,979 | B1 * | 2/2001 | Rittershaus et al. | 424/195.11 |
| 6,713,606 | B1 * | 3/2004 | Smith et al. | 530/350 |

FOREIGN PATENT DOCUMENTS

| WO | WO89/09220 | 10/1989 |
|---|---|---|
| WO | WO90/10385 | 9/1990 |
| WO | WO 91/05047 | 4/1991 |
| WO | WO91/05855 | 5/1991 |
| WO | WO97/11601 | 4/1997 |
| WO | WO/97/18307 | 5/1997 |
| WO | WO98/02454 | 1/1998 |
| WO | WO/98/39433 | 9/1998 |

OTHER PUBLICATIONS

Baxter SOLTRAN solution product #FKB4708G p. 1, 2001.*
Varty et al, "Response to organ shortage: kidney retrieval programme using non-heart beating donors," BMJ, 1994, vol. 308, p. 575, ABSTRACT.*
Candinas et al., Transpl Int. 9(1): 32037 (1996), PMID: 8748408 (Abstract).
Janβen et al., Transpl Int 16: 515-522 (2003).
Klaus et al., Transplantation Proceedings 39: 353-354 (2007).
Pratt et al., American Journal of Pathology 163(4): 1457-1465 (2003).
Stevens et al., American Journal of Transplantation 9: 1055-1062 (2009).
Bach et al., Immunol. Rev. 141: 5-30 (1994).
Blackshear, J. Biol. Chem. 288: 1501-1504 (1993).
Brasile et al., Transplant Proc. 19: 894-895 (1987).
Buysmann et al., Transplantation 64: 1620-1623 (1997).
Dupe et al., Thrombosis & Haemostasis 85(6): 695 (1991).
Fujino et al., J. Heart Lung Transplant 16: 1073-1080 (1997).
Hauet et al., Transplantation 64: 1082-1086 (1997).
Ho et al., Clin. Immunol. Immunopatrol. 80: 540-545 (1996).
Hourcade et al., J. Exp. Med. 168: 1255-1270 (1988).
Klickstein et al., J. Exp. Med. 165: 1095-1112 (1987).
Koyamada et al., Transplantation 65: 1210-1215 (1998).
Krych et al., FASEB J. 3(A): 368 (1989).
Krych et al., PNAS 88: 4353-4357 (1991).
Mclaughlin et al., TIBS 20: 272-276 (1994).
Mikata et al., Transplant Immunol. 2. 107-110 (1998).
Morgan, The Biological Effects of Complement Activation. In: Complement, Clinical Aspects And Relevant To Disease, Academic Press, London (1990).
Oberpenning et al., Nature Biotech., 17, 149-155 (1999).
Piddlersden et al., J. Immunol. 152. 5477-5484 (1994).
Pratt et al., Am. J. Pathol. 199: 2055-2066 (1996).
Pratt et al., Eur. J. Immunol. 27: 2848-2853 (1997).
Pruitt et al., J. Surg. Res. 50: 350-355 (1991).
Pruitt et al., Transplantation 52: 868-873 (1991).
Pruitt et al., Transplantation 57: 363-370 (1994).
Rossen et al., Circ. Res. 57: 119-130 (1985).
Sheerin et al., Curr. Opin. Nephrol. Hypertens 7: 305-310 (1998).
Weisman et al., Science. 249: 146-151 (1990).
Yeatman et al., Transplantation 65: 1084-1093 (1998).
Yeh et al., J. Immunol. 146: 250 (1991).
Hancock et al., Cell 63: 133-139 (1990).
Makrides et al., Journal of Biological Chemistry 267(34): 24754-24761 (1992).
Atherton et al., Solid Phase Peptide Synthesis, A Practical Approach, Chapter 3, pp. 25-37, IRL Press (1989).
Johnson, Current Opinion in Nephrology and Hypertension 6: 120-127 (1997).
Nangaku et al., J. Am. Soc. Nephrol. 10: 2323-2331 (1999).
Okabayashi et al., Ann. Thorac. Surg. 58: 50-56 (1994).

* cited by examiner

*Primary Examiner* — Hope A Robinson
(74) *Attorney, Agent, or Firm* — Perkins Coie LLP (57) ABSTRACT

This invention relates to formulations of polypeptides and their derivatives that act as inhibitors or regulators of the immune or coagulation systems and are of use in organ transplantation. It provides solutions which include, for example, complement inhibitors or regulators of T- or B-lymphocyte function in modified molecular forms that can be used to perfuse and modify organs prior to transplantation or to store organs prior to transplantation, and to localise agents on organs. It further provides for a preparation for perfusion of an organ prior to transplantation or storage of the organ comprising: a soluble derivative of a soluble polypeptide, said derivative comprising two or more heterologous membrane binding elements with low membrane affinity covalently associated with the polypeptide which elements are capable of interacting, independently and with thermodynamic additivity, with components of membranes of the organ exposed to extracellular perfusion fluids; and a physiologically acceptable flush storage solution.

4 Claims, 1 Drawing Sheet

METHOD OF PREPARING AN ORGAN BY PERFUSION

This application is a 371 of PCT/GB00/00834 filed on Mar. 8, 2000, which is hereby incorporated by reference.

This invention relates to formulations of polypeptides and their derivatives that act as inhibitors or regulators of the immune or coagulation systems and are of use in organ transplantation. The invention provides solutions which include, for example, complement inhibitors or regulators of T- or B-lymphocyte function in modified molecular forms that can be used to perfuse and modify organs prior to transplantation or to store organs prior to transplantation, and to localise agents on organs. The invention also relates to methods of making formulations according to the invention and to use of the formulations made. Where legally permissible, the invention also relates to methods of prevention, treatment or amelioration of a disease or disorder associated with inflammation, inappropriate complement activation or inappropriate activation of coagulant or thrombotic processes prior to, during, or after transplantation of an organ. For example, the invention provides methods of prevention, treatment or amelioration of hyperacute and acute allograft rejection of transplanted organs such as kidney, heart, liver or lungs (particularly in individuals sensitised by previously transplanted organs), ischaemia-reperfusion injury in transplanted organs, xenograft rejection and corneal graft rejection.

The term transplantation here indicates the placement of an organ, for example, a heart, a kidney or a lung, in a human or non-human animal patient. It also includes skin transplants, for example as might be necessary following severe burning. The purpose of replacement is to remove a diseased organ or tissue in the host and replace it with a healthy organ or tissue from the donor. The latter may be a recent cadaver, healthy volunteer or another animal species. Where the donor and the recipient are the same species the transplant is known as an allograft. Where the donor and the recipient are dissimilar species the transplant is known as a xenograft. The techniques necessary for transplantation are varied and depend to a large extent on the nature of the organ being transplanted; they have been developed in sufficient detail over the last few decades that transplantation in man is now a commonplace activity in the hospital setting. While the surgical operations may now be described as routine, the success of the transplant as a therapeutic modality depends on a number of possible physiological outcomes. For example, the host may reject the new organ via antibody-dependent hyperacute rejection mechanisms, cell-mediated acute rejection or chronic degenerative processes. All of these destructive processes may involve the activation of complement to some degree. In addition, it may not be possible to transplant a new organ retaining full vascular viability if, for example, the organ had deteriorated upon storage following removal from the donor.

The use of artificial bladders as transplants has also been reported (Oberpenning et al, 1999 Nature Biotechnology, 17, 149). In this instance, the artificial bladder was grown from individual bladder cells grown in the laboratory and then the cells were allowed to grow on an artificial support. When the 'new' bladder was deemed to be fully grown it was transplanted into dogs.

The complement system is composed of over 30 different proteins that are important in the response of the immune system to foreign antigens. The complement system becomes activated when its primary components are cleaved and the products alone or with other proteins, activate additional complement proteins resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or, for example, by lipopolysaccharides present in cell walls of pathogenic bacteria (the alternative pathway).

Complement activation is known to occur in a wide variety of acute inflammatory processes including those associated with ischaemia and reperfusion injury (Rossen et al, 1985 Circ. Res., 57, 119; Morgan B. P., 1990, The biological effects of complement activation. In 'Complement, Clinical Aspects and Relevance to Disease'. (Academic Press, London.).

The association of adverse complement activation with failure of transplants and/or grafts has been described by several authors. In studies of mouse-to-rat cardiac xenografts it was concluded that temporary suppression of complement activation induced long-term survival (Koyamada et al, 1998, Transplantation, 65 1210-5). Lung function in swine-to-primate xenotransplants was also improved when a complement regulator was used in the experimental model (Yeatman et al, 1998, Transplantation, 65, 1084-93). In a review, Sheerin and Sacks (Curr. Opin. Nephrol. Hypertens., 1998, 7, 305-10) elucidated the studies now being carried out on the role of complement in the pathogenesis of renal injury due to, among others, the transplant procedures; they concluded with the view that local complement synthesis was a potential target for complement-based therapy. This strategy was shared by Johnson (Transplantation, 1997, 6, 120-7) who also drew attention to the occurrence of complement activation during renal haemodialysis as well as xenotransplantation and the fact that complement inhibitors might be used to control the inflammation associated with complement activation. Adverse complement activation is not restricted to the xenogeneic transplant area but is also observed in allograft transplantation, including in HLA-identical matched individuals, where 10 percent of transplanted kidneys have been reported to be rejected by immunological mechanisms, mainly complement-mediated (Brasile et al 1987 Transplant Proc. 19 894-5). The activation of complement during transplantation may also be associated with thrombotic processes which may triggered by activation of endothelial cells (Bach et al, 1994, Immunol Rev. 141, 5-30).

Complement receptor type 1 (CR1) has been shown to be present on the membranes of erythrocytes, monocytes/macrophages, granulocytes, B cells, some T cells, splenic follicular dendritic cells, and glomerular podocytes. CR1 binds to the complement components C3b and C4b and has also been referred to as the C3b/C4b receptor. The structural organisation and primary sequence of one allotype of CR1 is known (Klickstein et al, 1987, J. Exp. Med. 165:1095-1112, Klickstein et al, 1988, J. Exp. Med. 168:1699-1717; Hourcade et 41988, J. Exp. Med. 168:1255-1270, WO 89/09220, WO 91/05047). It is composed of 30 short consensus repeats (SCRs) that each contain around 60-70 amino acids. In each SCR, around 29 of the average 65 amino acids are conserved. Each SCR has been proposed to form a three dimensional triple loop structure through disulphide linkages with the third and first and the fourth and second half-cystines in disulphide bonds. CR1 is further arranged as 4 long homologous repeats (LHRs) of 7 SCRs each. Following a leader sequence, the CR1 molecule consists of the N-terminal LHR-A, the next two repeats, LHR-B and LHR-C, and the most C-terminal LHR-D followed by 2 additional SCRs, a 25 residue putative transmembrane region and a 43 residue cytoplasmic tail.

Based on the mature CR1 molecule having a predicted N-terminal glutamine residue, hereinafter designated as residue 1, the first three SCR domains of LHR-A, referred to as SCR1, SCR2 and SCR3 herein, consist of residues 2-58, 63-120 and 125-191 respectively, of mature CR1.

Hourcade et al, 1988, J. Exp. Med. 168:1255-1270 observed an alternative polyadenylation site in the human CR1 transcriptional unit that was predicted to produce a secreted form of CR1. The mRNA encoded by this truncated sequence comprises the first 8.5 SCRs of CR1, and encodes a protein of about 80 kDa which was proposed to include the C4b binding domain. When a cDNA corresponding to this truncated sequence was transfected into COS cells and expressed, it demonstrated the expected C4b binding activity but did not bind to C3b (Krych et al., 1989, FASEB J. 3:A368; Krych et al, Proc. Nat. Acad. Sci. 1991, 88, 4353-7). Krych et al, also observed a mRNA similar to the predicted one in several human cell lines and postulated that such a truncated soluble form of CR1 with C4b binding activity may be synthesised in humans.

In addition, Makrides et al. (1992, J. Biol. Chem. 267 34 24754-61) have expressed SCR 1+2 and 1+2+3+4 of LHR-A as membrane-attached proteins in CHO cells. Moreover, short consensus repeats 8 to 11 of CR1 and the phosphatidyl anchor of Decay Accelerating Factor have been synthesised as a membrane bound stable expression construct in a swine endothelial cell line (Mikata S., et al, Transplant Immunol 1998 2 107-10). U.S. Pat. No. 5,847,082 describes chimaeric complement inhibitors comprising portions of the complement inhibitor CD59 and a transmembrane domain that serves to anchor the chimeric protein to the cell membrane while still retaining the complement inhibitory properties of the parent CD59 molecule. U.S. Pat. No. 5,843,778 describes chimeric proteins containing portions of the vaccinia complement control protein and a transmembrane domain as well as other related fusion proteins. In all these cases, however, the delivery of a complement inhibitor to a cell surface is dependent on the expression of the relevant transfected gene into that cell and occurs usually in the context of a transgenic animal.

Several soluble fragments of CR1 have also been generated via recombinant DNA procedures by eliminating the transmembrane region from the DNAs being expressed (WO 89/09220, WO 91/05047). The soluble CR1 fragments were functionally active, bound C3b and/or C4b and demonstrated Factor I cofactor activity depending upon the regions they contained. Such constructs inhibited in vitro complement-related functions such as neutrophil oxidative burst, complement mediated hemolysis, and C3a and C5a production. A particular soluble construct, sCR1/pBSCR1c, also demonstrated in vivo activity in a reversed passive Arthus reaction (WO 89/09220, WO 91/05047; Yeh et al, 1991, J. Immunol. 146:250), suppressed post-ischemic myocardial inflammation and necrosis (WO 89/09220, WO 91/05047; Weisman et al, Science, 1990, 249:146-1511; Dupe, R. et al, Thrombosis & Haemostasis (1991) 65(6) 695) and also blocked CNS inflammation, demyelination and deposition of complement components in a model of antibody-mediated demyelinating experimental allergic encephalomyelitis (ADEAE), (Piddlesden et al, 1994, J. Immunol. 152, 5477).

Soluble CR1 has been shown to inhibit complement-mediated rejection processes in various transplantation models (Pruitt & Bollinger, 1991, J. Surg. Res 50:350; Pruitt et al, 1991 Transplantation 52; 868, Pruitt et al, 1994, Transplantation 57, 363-370). This agent has also been shown to reduce vascular injury and microvascular thrombosis in renal allograft rejection in the rat. (Pratt et al, 1996, Am. J. Pathol. 149, 2055-2066; Pratt et al, 1997, Eur. J. Immunol, 27, 2848-2853).

The role of activated T lymphocytes in transplantation rejection is well established and is the basis for several immunosuppressive therapeutic approaches known to be useful in delaying graft rejection. These include agents such as cyclosporin, FK506 and rapamycin which are ligands for receptors termed cyclophilins or immunophilins and which intervene in cellular signalling pathways through inhibition of the phosphatase activity of calcineurin (see for example, Ho et al, 1996, Clin. Immunol. Immunopathol., 80, S40-5).

The use of the anti-CD3 monoclonal antibody OKT3 which can eliminate and inhibit CD3-positive T-cells is also relevant. That process may itself be linked to complement activation because renal allograft patients treated with the monoclonal antibody OKT3 had fewer side effects and less complement activation if the antibody was administered as a two-hour infusion rather than as a bolus infusion; the authors concluded that complement activation seemed to play a role in the development of side effects after the first OKT3 dose (Buysmann et al, 1997, Transplantation, 64, 1620-3).

WO 98/02454 describes water soluble derivatives of polypeptides which contain two or more heterologous membrane binding elements each of which has relatively low affinity for components of the outer cell membrane but which in combination give high affinity and relative selectivity for binding to outer membranes of different cell types.

The preferred derivatives of that invention have the following structure:

in which:

P is the soluble polypeptide, each L is independently a flexible linker group, each W is independently a peptidic membrane binding element, n is an integer of 1 or more and X is a peptidic or non-peptidic membrane-binding entity which may be covalently linked to any W.

Peptidic membrane binding elements are preferably located sequentially either at the N or C terminus of the soluble polypeptide and are preferably 8 to 20 amino acids long. The amino acid sequences are linked to one another and to the soluble peptide by linker groups which are preferably selected from hydrophilic and/or flexible aminoacid sequences of 4 to 20 aminoacids; linear hydrophilic synthetic polymers; and chemical bridging groups.

It has now been found that organs perfused with a novel formulation of an agent which is a soluble derivative of a soluble polypeptide that acts for example as an inhibitor or regulator of the immune or coagulation systems, which polypeptide or derivative has been modified according to WO98/02454 (such modifications including certain novel membrane binding elements), adsorb that agent and that the organ will retain the agent for prolonged periods. The perfused agent is thus capable of protecting an organ such as the kidney or an engineered tissue from complement attack without the need for expression of the protectant molecule in a transgenic animal or through gene therapy.

According to the invention there is provided a preparation for perfusion of an organ prior to transplantation or storage of the organ comprising: a soluble derivative of a soluble polypeptide, said derivative comprising two or more heterologous membrane binding elements with low membrane affinity covalently associated with the polypeptide which elements are capable of interacting, independently and with thermodynamic additivity, with components of membranes of the organ exposed to extracellular perfusion fluids; and a physiologically acceptable flush storage solution.

By "heterologous" is meant that the elements are not found in the native full length protein from which a soluble protein may be derived.

By "soluble polypeptide" is meant a truncated derivative of a full length protein which lacks its natural membrane binding capability, and/or a polypeptide which has a solubility level in aqueous media of >100 µg/ml.

By "membrane binding element with low membrane affinity" is meant that the element has only moderate affinity for membranes, that is a dissociation constant greater than 0.1 µM, preferably 1 µM-1 mM. The element preferably has a size <5 kDa.

The derivative should incorporate sufficient elements with low affinities for membrane components to result in a derivative with a high (preferably 0.01-10 nM dissociation constant) affinity for specific membranes. The elements combine so as to create an overall high affinity for the particular target membrane but the combination lacks such high affinity for other proteins for which single elements may be (low-affinity) ligands.

The elements should be chosen so as to retain useful solubility in pharmaceutical formulation media, preferably >100 µg/ml. Preferably at least one element is hydrophilic.

Preferably the polypeptide has anticoagulant, antithrombotic, or immunoregulatory activity. Examples of polypeptides having immunoregulatory activity are polypeptides with complement inhibitory activity. Preferably the polypeptide is a CR1 polypeptide fragment. Examples of preferred polypeptides having antithrombotic or anticoagulant activity are activated Protein C and hirudin and its analogues.

Also according to the invention there is provided a method for making a preparation according to the invention comprising: expressing DNA encoding the polypeptide portion of the derivative in a recombinant host cell; post-translationally modifying the polypeptide to chemically introduce the membrane binding elements to form the derivative; recovering the derivative; and mixing the derivative with the flush storage solution.

Methods according to the invention may further comprise: preparing a replicable expression vector capable, in the recombinant host cell, of expressing the DNA encoding the polypeptide; transforming the recombinant host cell with the vector; and culturing the transformed host cell under conditions permitting expression of the DNA polymer to produce the polypeptide.

Also according to the invention there is provided a method for preparing an organ prior to transplantation or storage of the organ comprising: making a preparation according to the invention; and perfusing the organ with the prepared solution.

Also according to the invention there is provided a method of prevention, treatment or amelioration of a disease or disorder associated with inflammation, inappropriate complement activation, or inappropriate activation of coagulant or thrombotic processes of an organ prior to, during or after transplantation or storage of the organ comprising: making a preparation according to the invention; and perfusing the organ with the preparation.

Also according to the invention there is provided a method of prevention, treatment or amelioration of a disease or disorder associated with inflammation, inappropriate complement activation or inappropriate activation of coagulant or thrombotic processes prior to, during or after transplantation of an organ comprising: preparing an organ according to the invention; and transplanting the perfused organ into an individual requiring a transplant of that organ.

Also according to the invention there is provided use of a preparation according to the invention in the prevention, treatment or amelioration of a disease or disorder associated with inflammation, inappropriate complement activation, or inappropriate activation of coagulant or thrombotic processes prior to, during or after transplantation or storage of an organ. Also according to the invention there is provided use of a preparation according to the invention in a method according to the invention.

The invention provides for localisation of therapeutic agents at cellular membranes of specific organs accessed by perfusion, thereby providing one or more of several biologically significant effects with potential therapeutic advantages including but not limited to inhibition of complement activation, inhibition of cytotoxic T lymphocyte function.

Flush storage solutions are used to flush organs prior to transplantation to prepare the graft for transplantation. They are designed to overcome the perceived problems associated with prolonged storage of organs. Flush storage solutions comprise sterile aqueous solutions with a pH, osmolarity and ionic composition compatible with the organ and take into consideration the metabolic activity and adenine nucleotide content of the organ during storage.

There are a number of commercially available flush storage solutions having different chemical compositions. The principle ones in use in the hospital setting are 'Euro-Collins', manufactured by Fresenius AG of Germany, 'VIASPAN®', made by Du Pont Chemical Company and 'Soltran' kidney perfusion solution, made by Baxter Healthcare Ltd, UK. In addition, there are a number of flush-storage solutions that have been described and which may be used at some time in the future in the hospital setting. These include those described in U.S. Pat. No. 5,702,881, based on a basal mammalian cell culture medium with specified additional excipients and those described in U.S. Pat. No. 5,693,462, which contains alternative excipients, notably amiloride-containing compounds.

Soltran from Baxter Healthcare Ltd contains the following constituents (per 1 L of solution):

Potassium citrate 8.6 g
Sodium citrate 8.2 g
Mannitol 33.8 g
Magnesium sulphate 10.0 g The solution has a pH of 7.1 and an osmolarity of 486 mOsm/L.

Saline solution close to isotonic (0.145M) may be used as a simple flush storage solution.

Various additions to flush storage solutions have been reported to improve organ survival and reduce reperfusion injury. These include pentoxifylline (Okabayashi et al, 1994, Ann Thorac. Surg. 58, 416-420), trimetazidine (Hauet et al, 1997, Tranplantation, 64, 1082-1086) and nitroprusside (Fujino et al, 1997, J. Heart Lung Transplant. 16, 1073-1080). In all these cases, the additions were made to flush storage solutions and the transplantation procedure involved transfer of some added agent to the recipient.

If the derivative is unstable in the flush storage solution the derivative may be stored separately from the flush storage solution in stable form and mixed with the flush storage solution shortly before the organ is perfused with the preparation.

Any soluble derivative of a soluble polypeptide, as herein defined, may be formulated with any flush storage solution.

In a preferred embodiment of the invention soluble derivatives of the soluble polypeptides described in U.S. Pat. No.

5,833,989 and WO 98/39433 are diluted in Soltran kidney perfusion solution. Also in a preferred embodiment of the invention the soluble derivatives described in WO 98/02454 are diluted in Soltran kidney perfusion solution.

In a further preferred embodiment of the invention soluble derivatives of soluble polypeptides described in WO 98/02454 and WO 98/39433 that contain the 'myristoyl electrostatic switch' sequence(s) as defined in WO 98/02454 and below are diluted in Soltran kidney perfusion solution. Membrane binding has been found to be associated with limited (single-site) modification with fatty acyl groups when combined with a cluster of basic amino acids in the protein sequence which may interact with acidic phospholipid head groups and provide the additional energy to target membrane binding. This combination of effects has been termed the "myristoyl-electrostatic switch" (S. McLaughlin and A. Aderem, TIBS, 20, 272-276, 1994; J. F. Hancock et al, Cell, 63, 133-139, 1990). Thus, a further example of suitable membrane binding elements are basic amino acid sequence such as those found in proteins such as Rad and MARCKS (myristoylated alanine-rich C-kinase substrate, P. J. Blackshear, J. Biol. Chem., 268, 1501-1504, 1993) which mediate the electrostatic "switch" through reversible phosphorylation of serine residues within the sequence and a concomitant neutralisation of the net positive charge. Such sequences include but are not restricted to consecutive sequences of Lysine or Arginine such as (Lys)n where n is from 3 to 10, preferably 4 to 7.

Suitable examples of amino acid sequences comprising basic amino acids include:
(i) DGPKKKKKKSPSKSSG (SEQ ID NO: 7)
(II) GSSKSPSKKKKKKPGD (SEQ ID NO: 8)
(iii) SPSNETPKKKKKRFSFKKSG (SEQ ID NO: 9)
(iv) DGPKKKKKKSPSKSSK (SEQ ID NO: 10)
(v) SKDGKKKKKKSKTK (SEQ ID NO: 11)
(N-terminus on left)

Sequences (I) to (v) are examples of electrostatic switch sequences.

In a more preferred embodiment of the invention the soluble derivative corresponding to SEQ ID No. 8 in WO 98/02454 (and provided here by way of reference as SEQ ID No. 1) is diluted in Soltran kidney perfusion solution.

In a further more preferred embodiment of the invention the soluble derivative corresponding to SEQ ID No. 2 is diluted in Soltran kidney perfusion solution.

In a further embodiment of the invention the soluble derivative corresponding to SEQ ID No. 3 is diluted in Soltran kidney perfusion solution.

In further embodiments of the invention polypeptide derivatives in which novel peptidic membrane binding elements are incorporated confer a high affinity for cell types found in the target organ. Examples of such cell types include glomerular epithelial and endothelial cells of the human kidney. These peptidic membrane binding elements W are ligands for cell surface proteins which act as markers for the particular organ or tissue.

It will be evident to the worker skilled in the art that different proteins can be formulated with different flush storage solutions to those exemplified above. For example, WO 98/02454 and WO 98/39433 describe several novel complement inhibitors that may be modified to form a soluble derivative and formulated in Soltran diluent. In addition, the Soltran diluent may be replaced by VIASPAN® or Euro-Collins flush-storage solutions described above.

The formulations of the invention are useful in the prevention, treatment or amelioration of many complement-mediated or complement-related disorders including, but not limited to hyperacute and acute allograft rejection of transplanted organs such as kidney, heart, liver or lungs (particularly in individuals sensitised by previously transplanted organs), ischaemia-reperfusion injury in transplanted organs, xenograft rejection and corneal graft rejection.

Figure 1:
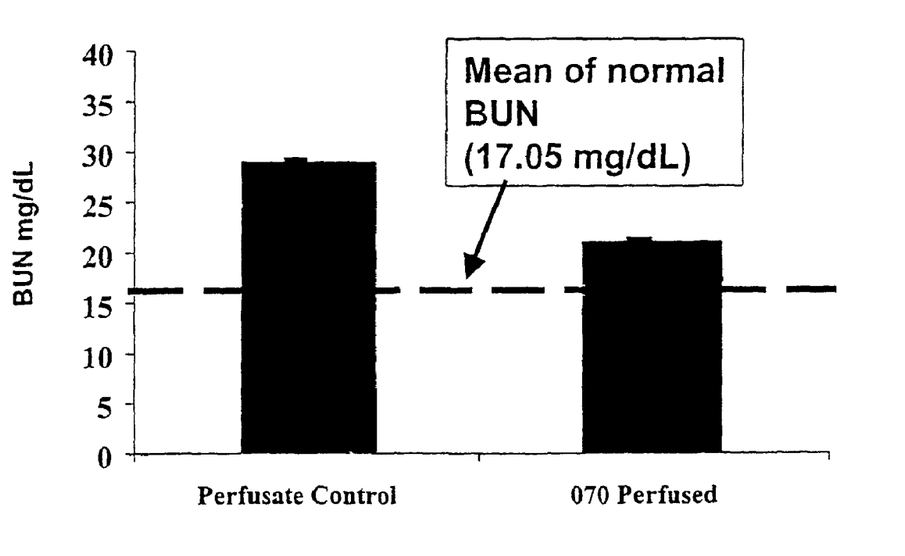
FIG. 1 shows blood urea nitrogen (BUN) data in DA-DA renal isograft receipients (n=6) at 2 weeks post transplant. The control group is significantly different (p<0.0001) form the normal, whereas the treated group is not significantly different from the normal (p=0.0530). The data shows that the organs perfused with a compound of the invention had improved renal function post transplantation during the first week post-transplantation.

The invention is further described by way of example.

GENERAL METHODS USED IN EXAMPLES (i) Sodium Dodecyl Sulphate Polyacrylamide Gel Electrophoresis (SDS PAGE)

SDS PAGE was carried out generally using the Novex system (Novex, Germany) according to the manufacturer's instructions. Prepacked gels of acrylamide concentrations 4-20% were most frequently used. Samples for electrophoresis, including protein molecular weight standards (for example LMW Kit, Pharmacia or Novex Mark 12) were usually diluted in 1% (w/v)SDS—containing buffer (with or without 5% (v/v) 2-mercaptoethanol), and left at room temperature for about 0.5 h before application to the gel.

(ii) Reduction of Disulphides and Modification of Thiols in Proteins

There are a number of methods used for achieving the title goals. The reason it may be necessary to carry out selective reduction of disulphides is that during refolding, concentration and further purification of multi-thiol proteins inappropriate disulphide pairing can occur. In addition, even if correct disulphide paring does occur, it is possible that a free cysteine in the protein may become blocked with the reducing agent, for example glutathione. These derivatives are generally quite stable. In order to make them more reactive, for example for subsequent conjugation to another functional group, they need to be selectively reduced, with for example dithiothreitol (DTT) or with Tris (2-carboxyethyl) phosphine.HCl (TCEP) then optionally modified with a function which is moderately unstable. An example of the latter is Ellmans reagent (DTNB) which gives a mixed disulphide. In the case where treatment with DTNB is omitted, careful attention to experimental design is necessary to ensure that dimerisation of the free thiol-containing protein is minimised. Reference to the term 'selectively reduced' above means that reaction conditions eg. duration, temperature, molar ratios of reactants have to be carefully controlled so that disulphide bridges within the natural architecture of the protein are not reduced. All the reagents are commercially available eg. from Sigma or Pierce.

The following general examples illustrate the type of conditions that may be used and that are useful for the generation of free thiols and their optional modification. The specific reaction conditions to achieve optimal thiol reduction and/or modification are ideally determined for each protein batch.

TCEP may be prepared as a 20 mM solution in 50 mM Hepes (approx. pH 4.5) and may be stored at −40 degrees C.

DTT may be prepared at 10 mM in sodium phosphate pH 7.0 and may be stored at −40 degrees C. DTNB may be prepared at 10 mM in sodium phosphate pH 7.0 and may be stored at −40 degrees C. All of the above reagents are typically used at molar equivalence or molar excess, the precise concentrations ideally identified experimentally. The duration and the temperature of the reaction are similarly determined experimentally. Generally the duration would be in the range 1 to 24 hours and the temperature would be in the range 2 to 30 degrees C. Excess reagent may be conveniently removed by buffer exchange, for example using Sephadex G25. A suitable buffer is 0.1M sodium phosphate pH7.0.

(iii) Anti-Complement Activity Measured by the Classical Pathway-Mediated Haemolysis of Sheep Erythrocytes Functional activity of complement inhibitors was assessed by measuring the inhibition of complement-mediated lysis of sheep erythrocytes sensitised with rabbit antibodies (Diamedix Corporation, Miami, USA). The assay is designed to be specific for the classical pathway of complement activation. Human serum diluted 1:100 (final concentration in assay mixture) in 0.1 M Hepes/0.15 M NaCl/0.1% gelatin pH 7.4 was used as a source of complement. The serum was prepared from a pool of volunteers essentially as described in Dacie & Lewis, 1975. Briefly, blood was warmed to 37° C. for 5 minutes, the clot removed and the remaining serum clarified by centrifugation. The serum fraction was split into small aliquots and stored at −196° C. or −80° C. Aliquots were thawed as required and diluted in the Hepes buffer immediately before use.

Inhibition of complement-mediated lysis of sensitised sheep erythrocytes was measured using a standard haemolytic assay using a v-bottom microtitre plate format as follows:

50 μl of a range of concentrations of inhibitor diluted in Hepes buffer were mixed with 50 μl of the diluted serum and 100 μl of sensitised sheep erythrocytes and then incubated for 1 hour at 37° C. Samples were spun at 1600 rpm at ambient temperature for 3 minutes before transferring 150 μl of supernatant to a flat bottom microtitre plate and determining the absorption at 405 or 410 nm. Maximum lysis (Amax) was determined by incubating serum with erythrocytes in the absence of any inhibitor. Background lysis (Ao) was determined by incubating erythrocytes in the absence of any serum or inhibitor. Inhibition was expressed as a fraction of the total cell lysis such that IH50 represents the concentration of inhibitor required to give 50% inhibition of lysis.

% inhibition=[1−[($A$−$Ao$)/($A$max−$Ao$)]]×100

(iv) Anti-Complement Activity Measured by Alternative Pathway-Mediated Haemolysis of Guinea Pig Erythrocytes Functional activity of complement inhibitors was assessed by measuring the inhibition of complement mediated lysis of guinea pig erythrocytes essentially as described by Scesney, S. M. et al (1996) J. Immunol. 26 1729-1735. The assay is designed to be specific for the alternative pathway of complement activation. Human serum prepared from a pool of volunteers essentially as described in Dacie & Lewis, 1975 was used as the source of complement. Briefly, blood was warmed to 37° C. for 5 minutes, the clot removed and the remaining serum clarified by centrifugation. The serum fraction was split into small aliquots and stored at −196° C. Aliquots were thawed as required and diluted in 0.1 M Hepes/0.15 M NaCl/ 0.1% gelatin/8 mM EGTA/5 mM MgCl$_2$ pH 7.4 (buffer A) immediately before use.

Guinea pig erythrocytes, as alsevers, were purchased from TCS Microbiology and were stored at +4 degrees C. They were used within 2 weeks.

50 μl of a range of concentrations of inhibitor diluted in buffer A in a v-bottom microtitre plate were mixed with, first, 100 μl of serum that had been diluted 1:3 (in Buffer A) and second, 50 μl of guinea pig erythrocytes (diluted 1:49 in buffer A) and incubated for 1 hour at 37° C. The plate was spun at 1600 rpm for 3 minutes before transferring 150 μl of each supernatant to a flat bottom microtitre plate and determining the absorption at 405 nm, which reflects the amount of lysis in each test solution. Maximum lysis (Amax) was determined by incubating serum with erythrocytes in the absence of any inhibitor. Background lysis (Ao) was determined by incubating erythrocytes in the absence of any serum or inhibitor. To check whether the inhibitor itself had any effect on lysis, erythrocytes were incubated with inhibitor alone; none of the compounds had any direct effect on lysis of the red blood cells. The final dilution of serum used in the assay did absorb at 405 nm but the level of absorbance (approx 10% of Amax) was considered to have a neglible affect on the overall assay results and it was ignored in the calculations. Inhibition was expressed as a fraction of the total cell lysis such that IH50 represents the concentration of inhibitor required to give 50% inhibition of lysis.

% inhibition=[1−[($A$−$Ao$)/($A$max−$Ao$)]]×100

Example 1

Synthesis and Isolation of a Membrane-Targeted Complement Inhibitor—SEQ ID No. 1 (Reference: WO 98/02454, Example 8)

a) Alternative Method for Further Purification

Purified SCR1-3/cys protein as defined in WO 98/02454, Example 6, (approx. 90 micromolar in phosphate-buffered saline (PBS); 87 ml) was treated with Triscarboxyethylphosphine (0.315 ml of 50 mM stock in 50 mM Hepes pH4.5) for 18 h at 25 degrees C. Ethanolamine was added to the solution to a final concentration of 0.05M by addition of 0.26 ml of undiluted stock reagent (assumed to be 16.6M). MSWP-1 (Example 2 in WO 98/02454) (2.35 ml of 10 mM stock in 0.1M sodium phosphate pH7.0) was added and the solution was incubated for a further 3 h at 25 degrees C. and then placed on ice for 15 min. 40 g of washed and suction-dried Toyopearl Butyl was added and the mixture was swirled and left for 5 min on ice. The mixture was swirled again and poured into a glass jacket of i.d., 41 mm and the matrix was developed as a normal chromatography, all at approx. 4 degrees C. The column was developed first with 0.1M sodium phosphate buffer and then with 0.3M ethanolamine. A major A280 peak was eluted from the matrix using the ethanolamine buffer. It was collected as a single fraction (40 ml) and was applied to a Sephadex G25 column (Vt 160 ml) that had been equilibrated with PBS. The fraction was chased through with equilibration buffer. The Vo fraction (70 ml) was regarded as the product and stored at −40 degrees C. By SDS PAGE followed by staining with Coomassie Brilliant Blue the Vo fraction contained a single major polypeptide of estimated purity >90% with an apparent molecular weight of 24000.

b) Alternative Purification Method II

The method was essentially as described in a) above but the buffer for the Sephadex G25 stage was PBS/50 mg ml$^{-1}$ mannitol USP/0.1M L-arginine BP pH 7.4. The adjustment of the pH was carried out by addition of HCl to the solution until the pH reached 7.4.

Example 2

Synthesis of a Myristoyl/Electrostatic Switch Peptide Reagent Incorporating Two Peptidic Membrane Binding Elements (SEQ ID NO: 3)

N-(Myristoyl)-Gly-Ser-Pro-Ser-Lys-Lys-Lys-Lys-Lys-Lys-Pro-Gly-Leu-Ser-Ser-Arg-Leu-Asp-Ala-(S-2-Thiopyridyl)Cys-NH$_2$ The peptide:
Gly-Ser-Pro-Ser-Lys-Lys-Lys-Lys-Lys-Lys-Pro-Gly-Leu-Ser-Ser-Arg-Leu-Asp-Ala-Cys-NH$_2$
(SEQ ID NO: 4)

was prepared using solid phase synthesis via the general Fmoc/tBu strategy developed by Sheppard and Atherton (E. Atherton and R. C. Sheppard, Solid Phase Synthesis, IRL Press, Oxford, 1989). Kieselguhr-supported polydimethylacrylamide resin (Macrosorb 100) was used as the solid support and was derivatised with ethylene diamine.

Coupling reactions were carried out using N-α-Fmoc protected reagents pre-activated with N,N'-diisopropylcarbodiimide/N-hydroxybenzotriazole (in 4-fold molar excess) with bromophenol blue monitoring. Fmoc cleavages used 20% piperidine in DMF. Reactions to assemble the peptide chain were carried out by repeated cycles of coupling and deprotection including the attachment of the modified Rink linkage reagent (p-[(R,S)-α-[1-(9H-fluoreny-9-yl-methoxyformamido] 2,4 dimethoxybenzyl]-phenoxyacetic acid) designed to yield a C-terminal amide on final cleavage. The side chain functionalities of the individual amino-acids were protected as follows:

Ser (tButyl), Lys (Boc), Asp (O-tButyl), Cys (Trityl).

On completion of the peptide assembly and with the peptide still attached to the resin, the myristoyl group was attached to the amino group of the N terminal glycine by direct coupling of myristic acid by the same activation procedure. This modified peptide was then cleaved from the resin and the side-chain protecting groups removed at the same time by treatment with trifluoracetic acid containing 2.5% water and 2.5% triisopropyl silane.

The crude product was treated with 2,2' dithiopyridine in 0.01M ammonium acetate solution at pH 8-9 for approx. 2 h, then acidified with acetic acid and purified by preparative high performance liquid chromatography (HPLC) in 0.1% trifluoracetic acid (TFA)/water and 0.1% TFA/acetonitrile as gradient component. After lyophilisation, the peptide was a white amorphous powder, soluble to at least 10 mg/ml in dimethylsulphoxide. Fast atom bombardment mass spectrometry gave main peaks at m/e 243.3.6 Daltons and 2455.6 Daltons corresponding to the monoprotonated and monosodiated molecular ions of the peptide. The 2-thiopyridyl content of the peptide was measured by dissolving it to 0.02 mM in 0.1M sodium phosphate pH 7.0 and reducing 0.003 ml by addition of 1 mM dithiothreitol (1.0 ml). The change in optical density at 343 nm was used to calculate the amount of pyridine 2-thione released using an extinction coefficient at this wavelength of 8080 cm$^{-1}$ M$^{-1}$. This indicated that the peptide content was approximately 47% of the dry weight. The two peptidic membrane binding elements in this molecule correspond to the cationic sequence Pro-Ser-Lys-Lys-Lys-Lys-Lys-Lys-Pro [SEQ ID No. 5] and the cell-binding sequence Leu-Ser-Ser-Arg-Leu-Asp-Ala [SEQ ID No. 6].

Example 3

Synthesis and Isolation of a Complement Inhibitor Protein Incorporating Two Peptidic Membrane Binding Elements SEQ ID No. 2 a) The synthesis and isolation of SCR1-3/cys has been described in detail before, in WO 98/02454, Example 6. Alternative methods for the isolation of purified protein have been carried out. The changes were principally ones to the refolding process and are disclosed in b) of this Example (below).

b) The isolation of SCR1-3/cys from E. coli inclusion bodies includes solubilisation of the cell pellet followed by chromatography on a cation exchange matrix, for example Macroprep High S. The alternative process for refolding referred to in a) above was:

Product from the ion-exchange column (approx. 3 mg total protein per ml; 400 ml) was buffer-exchanged at room temperature using Sephadex G25 Medium into 0.3M ethanolamine/1 mM EDTA/1 mM L-cysteine/1 mM L-cystine.2HCl (pH adjustment not required), collecting a 600 ml Vo volume. The Vo eluate was then diluted further into cold refold buffer to give a final dilution of 10-fold of the original volume applied to the G25 column. An additional 1 mM L-cystine.2HCl was added at 3 h and the solution was left static approx 2-3° C. for 3 d. (Later repeat experiments used the 2 mM L-cystine.2HCl concentration straight away rather than as two separate additions of 1 mM.)

The solution was then ultrafiltered using a YM10 membrane to a final retentate volume of about 200 ml, which was mixed with 9 vol. 0.1M NaH$_2$PO$_4$/1M (NH$_4$)$_2$SO$_4$ pH 7.0 (Buffer A) at room temperature and immediately centrifuged at 3000 rpm for 20 min. The supernatant from the centrifugation was then chromatographed at room temperature on Toyopearl Butyl 650M and target protein eluted using a gradient (developed over 1 bed volume) of Buffer A to 0.1M sodium phosphate pH7.0. A single major A280 peak was evident during the gradient elution and this was collected separately and was regarded as the product.

c) Conjugation of SCR1-3/cys and MSWP Reagent.

The synthesis of the conjugate followed the same methodology as described previously for similar conjugates using alternative MSWP reagents, for example as described in Example 1 above, except that the MSWP reagent described in Example 2 was used. The synthesis was judged to be successful on the basis of analysis of the post reaction samples by SDS PAGE followed by staining for protein with Coomassie Brilliant Blue, which showed a shift in mobility of the SCR1-3/cys (apparent molecular weight 22000) to a slightly higher molecular weight (24000), consistent with the addition of the MSWP reagent in a 1:1 molar ratio. The product of the reaction was formulated by buffer-exchange into PBS/50 mg per ml mannitol/0.1M L-arginine.HCl, adjusted to pH 7 with hydrochloric acid. The product had a protein concentration of 2.3 mg/ml, based on A280 and a molar extinction coefficient of 30000. The product exhibited anti-haemolytic activity in classical pathway (IH50=0.3 nM) and alternative pathway (IC50=100 nM) haemolytic assays in vitro. Details of the two haemolytic assays have been described previously and are given in General methods.

d) Further purification and initial formulation into PBS/mannitol/arginine buffer. Target protein (63 mg) synthesised in a similar way to that described in c) above, but not buffer-exchanged, was diluted 20-fold (total volume 700 ml) into 0.1M sodium phosphate/1M ammonium sulphate pH 7.0. The solution was then mixed batch-wise at 4° C. with 35 g of suction-dried Macroprep Methyl and then poured directly into a glass jacket and the matrix developed as a normal chromatography. The matrix was washed with 0.1M sodium phosphate/1M ammonium sulphate pH 7.0 until the baseline stabilised and then the target protein was eluted using 0.3M ethanolamine. The A280 peak containing the protein was collected and it was immediately buffer-exchanged acid using Sephadex G25 into PBS/50 mg per ml mannitol (USP)/ 0.1M L-arginine (USP), adjusted to pH 7 with hydrochloric acid. The product had a protein concentration of 0.3 mg/ml, based on A280 and a molar extinction coefficient of 30000. The Vo fraction of the G25 column was pooled with a similar product and it was ultrafiltered (YM10 membrane; Amicon) to an approx. 15-fold concentrate. The retentate was then passed through a 0.2 micron filter (Sartorius, NMWL) and the filtrate was aliquoted and frozen. This material was regarded as the product. The product had a protein concentration of 4.0 mg/ml, based on A280 and a molar extinction coefficient of 30000. Purity determined by non-reduced SDS PAGE followed by staining for protein using Coomassie Brilliant Blue showed that about 95% of the stainable protein had an apparent molecular weight of about 23000—this was target modified protein. Visible contaminants included protein dimer, with an apparent molecular weight of about 37000, and unmodified protein, with an apparent molecular weight of about 21000. The product exhibited anti-haemolytic activity in classical pathway (IH50=0.1 nM) and alternative pathway (IC50=100 nM) haemolytic assays in vitro. Details of the two haemolytic assays have been described previously and are given in General methods.

Example 4

Formulation of the Complement Inhibitor of Example 1 in Soltran Kidney Perfusion Solution Material prepared as described in Example 1b) above was lyophilised from the PBS/mannitol/arginine buffer described in Example 3d above. It was resolubilised to the original volume in water and then diluted into Soltran perfusate resulting in a solution with a concentration of about 200 µg/ml. (~8 µM) The solution was used immediately.

Example 5

Formulation of the Complement Inhibitor of Example 3 in Soltran Kidney Perfusion Solution Material prepared as described in Example 3c above (0.01 ml) was diluted into Soltran perfusate (0.99 ml).). It resulted in a solution with a concentration of about 0.02 mg/ml (0.87 µM). The solution was then stored frozen at −40 degrees C. 5 days later it was thawed and it was assayed in the classical pathway haemolytic assay (General method no. 3); it exhibited an IH50 of 0.2 nM, indicating that it had retained full activity.

Example 6

Method for the Perfusion of a Kidney with Complement Inhibitors of the Invention A donor rat kidney was isolated and extracted from the animal using standard anaesthetic and surgical procedures. The organ was removed with the entire renal artery and a portion of the aorta intact but ligated at the anterior end. The renal vein was cut at an appropriate point for subsequent transplantation procedure. Complement inhibitors diluted in carrier solutions as described above (approximately 2 ml) were then administered through the isolated organ by slow injection into the lumen of the aorta. Care was taken to avoid delivery of air bubbles into the organ vasculature during this procedure. Solutions administered in this way perfuse the kidney and emerge from the renal vein.

Example 7

Method for the Transplantation of Kidneys and Experimental Evaluation of Retention of Complement Inhibitors by Immunofluorescence The kidney of a recipient rat was removed and the donor kidney prepared as in Example 6 positioned in its place. The segment of aorta used to enable perfusion of the organ was removed and the renal artery cut to an appropriate length. The donor and recipient artery, vein and ureter were then joined end to end by standard microvascular surgical techniques returning blood flow to the donor organ and allowing urine drainage. To evaluate the retention of complement inhibitors within the organ, perfused transplanted organs were removed at various time points post-transplantation and immediately frozen at −196° C. Frozen sections 4 µm thick were prepared from such tissues and incubated at 4° C. for one hour with the appropriate volumes of a fluorescent-labelled murine monoclonal antibody (C-3 conjugated 3E10 at 0.47 mg/ml in phosphate-buffered saline) raised against the bacterially expressed first 3 short consensus repeats of human CR1. Photomicrography of sections under ultraviolet light revealed that exposure of rat kidneys to compounds such as Example 3 above and Example 8 of WO98/02454 resulted in immunofluorescent delineation of the vascular and parenchymal structures of the organ and that this labelling persisted when the kidneys were transplanted into recipient animals.

Example 8

Method for the Transplantation of Kidneys and Experimental Evaluation of the Effect of Complement Inhibitors in the First Week Post Transplant The kidney of a recipient rat was removed and the donor kidney prepared as in Example 6 positioned in its place. The segment of aorta used to enable perfusion of the organ was removed and the renal artery cut to an appropriate length. The donor and recipient artery, vein and ureter were then joined end-to-end by standard microvascular surgical techniques returning blood flow to the donor organ and allowing urine drainage. To evaluate the effect of compounds as in Example 1 above within the organ, perfused transplanted organs were removed at various time points post-transplantation, portions of which were either frozen at −196° C. or fixed in a 4% formaldehyde solution in saline. Sections of frozen tissues 4 µm thick were stained with a mouse anti-rat C5b-9 neoantigen antibody (a gift from Dr W. Couser, University of Washington, Seattle, USA; published in: Nangaku M. Pippin J. Couser W G. Journal of the American Society of Nephrology. 10(11):2323-31, 1999 Nov.) and visualised with an anti-mouse Ig antibody conjugated to FITC (Dako). Formal/saline fixed tissues were processed and embedded in paraffin wax blocks using standard methods. Sections of these tissues 2 µm thick were stained by Haemotoxylin and Eosin, and Periodic Acid Schiffs stains using standard methods (Theory and Practice of Histological Techniques, Ed. John D. Bancroft and Alan Stevens, 3rd Edition, Churchill Livingstone, London, 1990). Such staining revealed histopathological evidence that organs perfused with the compound of Example 1 at a concentration of 40 micrograms/ml and using the perfusion method of Example 6 and the transplantation method of Example 7 above had reduced complement activation and reduced tissue injury compared to organs not perfused with membrane-targeted inhibitors of complement activation. Blood samples taken from the tail tip of recipients of perfused and transplanted donor kidneys at each day post transplant were analysed for urea nitrogen content as a marker of renal function using a commercially available kit (Sigma UK). Data from analysis of such samples gave evidence that organs perfused with the compound of Example 1 had improved renal function post transplantation during the first week post-transplantation.

Example 9

Method for the Transplantation of Kidneys and Experimental Evaluation of the Effect of Complement Inhibitors Over 20 Weeks Post Transplant The first kidney of a recipient rat was removed and the donor kidney prepared as in Example 6 positioned in its place. The segment of aorta used to enable perfusion of the organ was removed and the renal artery cut to an appropriate length. The donor and recipient artery, vein and ureter were then joined end-to-end by standard microvascular surgical techniques returning blood flow to the donor organ and allowing urine drainage. Seven days after the primary transplantation, the first kidney of the recipient rat was removed thus rendering the recipient dependent for renal function on the transplanted test organ. To evaluate the effect of the compound of Example 1 within the organ, perfused transplanted organs were removed at 20 weeks post-transplantation portions of which were fixed in a 4% formaldehyde solution in saline. Formal/saline fixed tissues were processed and embedded in paraffin wax blocks using standard methods. Sections of these tissues 2 μm thick were stained by Haemotoxylin and Eosin, and Periodic Acid Schiffs stains using the standard methods noted in Example 8. Such staining revealed histopathological evidence that organs perfused with the compound of Example 1 and transplanted as in Example 6 and 7 above had reduced tissue injury compared to organs perfused with a solution lacking the membrane-targeted complement inhibitor. Blood samples taken from the recipients of perfused and transplanted donor kidneys at regular time intervals over 20 weeks post transplant were analysed for urea nitrogen content as a marker of renal function using a commercially available kit (Sigma UK). Data from analysis of such samples gave evidence that organs perfused with the compound of Example 1 had improved renal function post transplantation over 20 weeks post-transplantation.

In the foregoing description, where reference has been made to prior publications, published patents and patent applications, the content thereof is incorporated herein by reference.

The invention claimed is:

1. A method for preparing an organ by perfusion prior to transplantation or storage of the organ comprising:
   providing a preparation to ameliorate ischemic reperfusion injury; and
   perfusing an organ prior to transplantation or storage of the organ, wherein the preparation comprises:
   i) a soluble polypeptide that has the amino acid sequence of SEQ ID NO:1 or
   ii) a soluble polypeptide consisting of the amino acid sequence of amino acids 2-197 and 199-215 of SEQ ID NO:1, wherein the soluble polypeptide is conjugated to myristoyl; and wherein perfusion comprises a non-reducing flush storage solution, wherein the flush storage solution is a perfusion solution; that comprises potassium citrate, sodium citrate, mannitol, and magnesium sulphate; and wherein the preparation maintains the complement inhibitor activity of the soluble polypeptide.

2. The method according to claim 1, wherein the organ is a kidney, a heart, a liver, or a lung.

3. The method according to claim 2, wherein the organ is a human organ.

4. The method according to claim 2, wherein the organ is a non-human animal organ.

* * * * *

```
                              SEQUENCE LISTING

<160> NUMBER OF SEQ ID NOS: 11

<210> SEQ ID NO 1
<211> LENGTH: 215
<212> TYPE: PRT
<213> ORGANISM: Artificial Sequence
<220> FEATURE:
<223> OTHER INFORMATION: Linear, 2 polypeptide chains disulphide linked
<221> NAME/KEY: DISULFID
<222> LOCATION: (198)..(199)
<223> OTHER INFORMATION: 2nd polypeptide chain (199-215) runs C to N
      terminus
<223> OTHER INFORMATION: An N-myristoyl group is at the N-terminus of
      the second polypeptide chain
<223> OTHER INFORMATION: A CONH2 group is at the C terminus of the
      second polypeptide chain
<223> OTHER INFORMATION: Description of Artificial Sequence: Synthetic
      peptide reagent

<400> SEQUENCE: 1

Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
             20                  25                  30

Cys Arg Pro Gly Tyr Ser Gly Arg Pro Phe Ser Ile Ile Cys Leu Lys
         35                  40                  45

Asn Ser Val Trp Thr Gly Ala Lys Asp Arg Cys Arg Arg Lys Ser Cys
     50                  55                  60

Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                 85                  90                  95
```

```
Leu Ile Gly Ser Ser Ser Ala Thr Cys Ile Ile Ser Gly Asp Thr Val
            100                 105                 110

Ile Trp Asp Asn Glu Thr Pro Ile Cys Asp Arg Ile Pro Cys Gly Leu
            115                 120                 125

Pro Pro Thr Ile Thr Asn Gly Asp Phe Ile Ser Thr Asn Arg Glu Asn
            130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys Cys Cys Asp Gly Pro Lys Lys Lys Lys Lys Lys
            195                 200                 205

Ser Pro Ser Lys Ser Ser Gly
210                 215
```

<210> SEQ ID NO 2
<211> LENGTH: 218
<212> TYPE: PRT
<213> ORGANISM: Artificial Sequence
<220> FEATURE:
<223> OTHER INFORMATION: 2 polypeptide chains disulphide linked
<221> NAME/KEY: DISULFID
<222> LOCATION: (198)..(199)
<223> OTHER INFORMATION: The second polypeptide chain (199-218) runs C
      to N terminus
<223> OTHER INFORMATION: An N-Myristoyl group is at the N terminus of
      the second polypeptide chain
<223> OTHER INFORMATION: A CONH2 group is at the C terminus of the
      second polypeptide chain
<223> OTHER INFORMATION: Description of Artificial Sequence: Synthetic
      peptide reagent

<400> SEQUENCE: 2

```
Met Gln Cys Asn Ala Pro Glu Trp Leu Pro Phe Ala Arg Pro Thr Asn
1               5                   10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
50                  55                  60

Arg Asn Pro Pro Asp Pro Val Asn Gly Met Val His Val Ile Lys Gly
65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
            100                 105                 110

Ile Trp Asp Asn Glu Thr Pro Ile Cys Asp Arg Ile Pro Cys Gly Leu
            115                 120                 125

Pro Pro Thr Ile Thr Asn Gly Asp Phe Ile Ser Thr Asn Arg Glu Asn
            130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
```

```
                180             185              190
Ile Ile Pro Asn Lys Cys Cys Ala Asp Leu Arg Ser Ser Leu Gly Pro
        195                 200                 205
Lys Lys Lys Lys Lys Lys Ser Pro Ser Gly
    210                 215

<210> SEQ ID NO 3
<211> LENGTH: 20
<212> TYPE: PRT
<213> ORGANISM: Artificial Sequence
<220> FEATURE:
<223> OTHER INFORMATION: An N-myristoyl group is at the N terminus of
      the polypeptide chain
<223> OTHER INFORMATION: A CONH2 group is at the C-terminus of the
      polypeptide chain
<223> OTHER INFORMATION: An S-2-Thiopyridyl group is attached to the
      C-terminal cysteine
<223> OTHER INFORMATION: Description of Artificial Sequence: Synthetic
      peptide reagent

<400> SEQUENCE: 3

Gly Ser Pro Ser Lys Lys Lys Lys Lys Pro Gly Leu Ser Ser Arg
 1               5                  10                  15

Leu Asp Ala Cys
            20

<210> SEQ ID NO 4
<211> LENGTH: 20
<212> TYPE: PRT
<213> ORGANISM: Artificial Sequence
<220> FEATURE:
<223> OTHER INFORMATION: A CONH2 group is at the C terminus
<223> OTHER INFORMATION: Description of Artificial Sequence: Synthetic
      peptide

<400> SEQUENCE: 4

Gly Ser Pro Ser Lys Lys Lys Lys Lys Pro Gly Leu Ser Ser Arg
 1               5                  10                  15

Leu Asp Ala Cys
            20

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: A peptidic
      membrane binding element of SEQ ID NO: 4

<400> SEQUENCE: 5

Pro Ser Lys Lys Lys Lys Lys Lys Pro
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: A peptidic
      membrane binding element of SEQ ID NO: 4

<400> SEQUENCE: 6

Leu Ser Ser Arg Leu Asp Ala
 1               5

<210> SEQ ID NO 7
```

-continued

```
<211> LENGTH: 16
<212> TYPE: PRT
<213> ORGANISM: Artificial Sequence
<220> FEATURE:
<223> OTHER INFORMATION: Description of Artificial Sequence: Example of
      electrostatic switch sequence

<400> SEQUENCE: 7

Asp Gly Pro Lys Lys Lys Lys Lys Ser Pro Ser Lys Ser Ser Gly
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Example of
      electrostatic switch sequence

<400> SEQUENCE: 8

Gly Ser Ser Lys Ser Pro Ser Lys Lys Lys Lys Lys Pro Gly Asp
 1               5                  10                  15

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Example of
      electrostatic switch sequence

<400> SEQUENCE: 9

Ser Pro Ser Asn Glu Thr Pro Lys Lys Lys Lys Arg Phe Ser Phe
 1               5                  10                  15

Lys Lys Ser Gly
            20

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Example of
      electrostatic switch sequence

<400> SEQUENCE: 10

Asp Gly Pro Lys Lys Lys Lys Lys Ser Pro Ser Lys Ser Ser Lys
 1               5                  10                  15

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Example of
      electrostatic switch sequence

<400> SEQUENCE: 11

Ser Lys Asp Gly Lys Lys Lys Lys Lys Ser Lys Thr Lys
 1               5                  10
```